(12) United States Patent
Kang et al.

(10) Patent No.: US 9,263,160 B2
(45) Date of Patent: Feb. 16, 2016

(54) COLLIMATOR MODULE, RADIATION DETECTOR HAVING COLLIMATOR MODULE, RADIOLOGICAL IMAGING APPARATUS HAVING COLLIMATOR MODULE, AND CONTROL METHOD OF RADIOLOGICAL IMAGING APPARATUS

(71) Applicant: SAMSUNG ELECTRONICS CO., LTD., Suwon-si, Gyeonggi-do (KR)

(72) Inventors: Ji Hoon Kang, Hwaseong-si (KR); Byung Sun Choi, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 224 days.

(21) Appl. No.: 14/025,118

(22) Filed: Sep. 12, 2013

(65) Prior Publication Data
US 2014/0119508 A1    May 1, 2014

(30) Foreign Application Priority Data

Oct. 31, 2012    (KR) .......................... 10-2012-0121968

(51) Int. Cl.
*A61B 6/00*    (2006.01)
*A61B 6/03*    (2006.01)
*G21K 1/02*    (2006.01)
(Continued)

(52) U.S. Cl.
CPC . *G21K 1/025* (2013.01); *A61B 6/06* (2013.01); *A61B 6/4233* (2013.01); *G21K 1/04* (2013.01); *A61B 6/032* (2013.01); *A61B 6/54* (2013.01)

(58) Field of Classification Search
CPC .......... A61B 6/032; A61B 6/035; A61B 6/06; A61B 6/54; A61B 6/542; A61B 6/545; G21K 1/02; G21K 1/025; G21K 1/04; G21K 1/10

USPC ............................................ 378/19, 147–155
See application file for complete search history.

(56) References Cited

U.S. PATENT DOCUMENTS 2,138,555 A * 11/1938 Otvos ............................ 378/155
3,869,615 A *  3/1975 Hoover et al. ................ 378/146
(Continued)

FOREIGN PATENT DOCUMENTS

JP         11-30670       2/1999
JP       2005-172477      6/2005

OTHER PUBLICATIONS

Korean Office Action dated Jul. 23, 2014 in Korean Patent Application No. 10-2012-0121968, 6 pages.
(Continued)

*Primary Examiner* — Allen C. Ho
(74) *Attorney, Agent, or Firm* — Staas & Halsey LLP

(57) ABSTRACT

A collimator module which may be disposed in a radiation detector of a radiological imaging apparatus using the collimator module may include a first collimator having a plurality of openings, through which radiation having passed through an object passes, and a second collimator located below the first collimator and having a plurality of openings, through which radiation having passed through the first collimator passes. The first collimator or the second collimator is designed so as to be movable or rotatable relative to the second collimator or the first collimator. Through movement of the first collimator or the second collimator, the size of a passage region that allows radiation having passed through the object to pass through the first collimator or the second collimator is adjustable.

40 Claims, 19 Drawing Sheets

(51) Int. Cl.
*G21K 1/04* (2006.01)
*A61B 6/06* (2006.01)

(56) References Cited

U.S. PATENT DOCUMENTS

| | | | | |
|---|---|---|---|---|
| 4,651,002 | A | * | 3/1987 | Anno .................... 250/336.1 |
| 4,731,806 | A | * | 3/1988 | Takahata ................. 378/155 |
| 5,231,655 | A | * | 7/1993 | Wei et al. ................. 378/147 |
| 5,233,193 | A | * | 8/1993 | Arakawa .................. 250/580 |
| 5,461,653 | A | * | 10/1995 | Parker ....................... 378/22 |
| 5,606,589 | A | * | 2/1997 | Pellegrino et al. ......... 378/154 |
| 6,185,278 | B1 | * | 2/2001 | Appleby et al. ............ 378/149 |
| 6,266,393 | B1 | * | 7/2001 | Ein-Gal ..................... 378/152 |
| 6,526,123 | B2 | * | 2/2003 | Ein-Gal ..................... 378/152 |
| 6,987,836 | B2 | * | 1/2006 | Tang ................... G21K 1/025 378/147 |
| 7,787,596 | B2 | * | 8/2010 | Hempel et al. ............. 378/154 |
| 2003/0012341 | A1 | | 1/2003 | Danielsson |
| 2005/0263717 | A1 | | 12/2005 | Soluri et al. |

OTHER PUBLICATIONS

Korean Office Action dated Nov. 8, 2013 from Korean Patent Application No. 10-2012-0121968, 12 pages.

* cited by examiner

COLLIMATOR MODULE, RADIATION DETECTOR HAVING COLLIMATOR MODULE, RADIOLOGICAL IMAGING APPARATUS HAVING COLLIMATOR MODULE, AND CONTROL METHOD OF RADIOLOGICAL IMAGING APPARATUS

CROSS-REFERENCE TO RELATED APPLICATIONS

This application claims the priority benefit of Korean Patent Application No. 10-2012-0121968, filed on Oct. 31, 2012 in the Korean Intellectual Property Office, the disclosure of which is incorporated herein by reference for all purposes.

BACKGROUND

1. Field

Embodiments disclosed herein relate to a collimator module, a radiation detector, a radiological imaging apparatus, and a control method of the radiological imaging apparatus.

2. Description of the Related Art

Radiation, e.g. X-rays, emitted to a particular material may pass through the material, or may be absorbed, in a predetermined amount, by the material, according to internal properties of the material, e.g., a density of the material.

A radiological imaging apparatus may refer to an imaging system that acquires a 2D or 3D image of internal tissues or structures of a particular material using radiation-transmission or radiation-absorption properties of the material. The radiological imaging apparatus is adapted to generate an image upon receiving radiation having passed through the particular material. Examples of the radiological imaging apparatus include an X-ray imaging apparatus, a Computed Tomography (CT) apparatus, and a Full Field Digital Mammography (FFDM) apparatus.

Considering an operation principle of the radiological imaging apparatus, if radiation generated from a radiation emitter of the radiological imaging apparatus is emitted to an object such as a human body, a radiation detector receives some of the radiation emitted to the object except for radiation absorbed by various internal materials of the object. That is, the radiation detector may receive radiation having passed through the object or emitted to the vicinity of the object. The radiation detector changes the received radiation into electric signals and stores the electric signals in a storage element, for example, a capacitor. An image processor of the radiological imaging apparatus reads out the electric signals stored in the storage element to generate a radiological image, and a display device, such as a monitor, displays the radiological image to the user.

As such, the user may check or examine the internal tissues, structures, or materials of the object via images.

The radiological imaging apparatus, which provides images of the internal tissues or structures of the object as described above, may be used to assist a doctor or other user in detecting abnormalities, such as diseases, in a human body, to recognize the internal configuration of mechanical elements in industrial applications, to scan the interior of luggage in the airport, and the like.

SUMMARY

It is an aspect of the present invention to provide a collimator module including a plurality of collimators, a radiation detector using the collimator module, and a radiological imaging apparatus using the collimator module, which enable detection of appropriate radiation according to a desired imaging purpose.

It is another aspect of the present invention to change the size of a radiation passage region of a collimator module via displacement of at least one collimator among a plurality of collimators stacked one above another, thereby allowing appropriate radiation to be introduced to a radiation detector.

It is another aspect of the present invention to provide a radiological image with a sensitivity or resolution optimized for a desired imaging purpose by adjusting the quantity of radiation to be introduced to a radiation detector.

It is a further aspect of the present invention to provide a radiological imaging apparatus provided with a collimator module, for example, a computed tomography apparatus, thereby adjusting the generation or emission quantity of radiation and the position of the collimator module according to a desired imaging purpose, resulting in less radiation exposure (for example, less radiation being exposed to a patient's body).

Additional aspects of the invention will be set forth in part in the description which follows and, in part, will be apparent from the description, or may be learned by practice of the invention.

In accordance with one aspect of the invention, a collimator module includes a first collimator having a plurality of openings, through which radiation having passed through an object passes, and a second collimator having a plurality of openings, through which radiation having passed through the first collimator passes. Here, the first collimator or the second collimator may be movable (rotatable) relative to the other collimator, i.e. the second collimator or the first collimator.

In this case, the size of a passage region that allows radiation having passed through the object to pass through the first collimator or the second collimator may be adjusted according to movement of the first collimator or the second collimator.

The first collimator or the second collimator may be movable such that some of the openings of the first collimator and some of the openings of the second collimator overlap each other.

The first collimator or the second collimator may be moved toward or away from the second collimator or the first collimator.

The openings of the first collimator or the second collimator may be separated from one another by partitions. The openings of the first collimator and the second collimator may have the same size, or may have different sizes.

The openings of the first collimator and the second collimator may have a width within a range of about 0.5 mm to about 10 mm, and a height within a range of about 1 mm to about 40 mm.

In accordance with another aspect of the present invention, a collimator module includes a plurality of collimators having a plurality of openings through which radiation having passed through an object passes, the plurality of collimators being stacked one above another to allow the radiation to sequentially pass through the plurality of openings, and at least one collimator among the plurality of collimators being movable relative to another collimator.

In accordance with another aspect of the present invention, a radiation detector, adapted to receive radiation emitted from a radiation emitter, includes a first collimator having a plurality of openings, through which radiation having passed through the object passes, a second collimator having a plurality of openings, through which radiation having passed through the first collimator passes, and a sensor that senses radiation having passed through the first collimator and the second collimator and changes the sensed radiation into electric signals. Here, the first collimator or the second collimator may be movable relative to the second collimator or the first collimator.

The size of a passage region that allows radiation having passed through the object to pass through the first collimator or the second collimator may be adjusted according to movement of the first collimator or the second collimator.

The first collimator or the second collimator may be movable relative to the second collimator or the first collimator such that some of the openings of the first collimator and some of the openings of the second collimator overlap each other, and the first collimator or the second collimator may be moved toward or away from the second collimator or the first collimator.

In accordance with another aspect of the present invention, a radiological imaging apparatus includes a plurality of collimators having a plurality of openings through which radiation having passed through an object passes, and a sensor that senses radiation having passed through the plurality of collimators and changes the radiation into electric signals, the plurality of collimators being stacked one above another to allow the radiation to sequentially pass through the plurality of openings, and at least one collimator among the plurality of collimators being movable relative to another collimator.

In accordance with another aspect of the present invention, a radiological imaging apparatus includes a radiation emitter to emit radiation to an object, a first collimator having a plurality of openings, through which radiation having passed through an object passes, a second collimator having a plurality of openings, through which radiation having passed through the first collimator passes, a sensor that senses radiation having passed through the first collimator and the second collimator and changes the sensed radiation into electric signals, an image processor that generates a radiological image based on the electric signals changed by the sensor, and a controller that controls movement of at least one of the first collimator or the second collimator.

The controller may control movement of at least one of the first collimator or the second collimator according to the object to be imaged, an imaging area of the object, or a preset imaging mode.

The size of a passage region that allows radiation having passed through the object to pass through the first collimator or the second collimator may be adjusted according to movement of the first collimator or the second collimator.

The first collimator or the second collimator may be movable relative to the second collimator or the first collimator such that some of the openings of the first collimator and some of the openings of the second collimator overlap each other. The first collimator or the second collimator may be moved toward or away from the second collimator or the first collimator.

The image processor may generate a radiological image corresponding to one pixel based on the electric signals derived from radiation having passed through the same openings of the first and second collimators.

In accordance with a further aspect of the present invention, a radiological imaging apparatus includes a radiation emitter to emit radiation to an object, a plurality of collimators having a plurality of openings through which radiation having passed through the object passes, and a sensor that senses radiation having passed through the plurality of collimators and changes the sensed radiation into electric signals, and an image processor that generates a radiological image based on the electric signals from the sensor, the plurality of collimators being stacked one above another to allow the radiation to sequentially pass through the plurality of openings, and at least one collimator among the plurality of collimators being movable relative to another collimator.

The radiological imaging apparatus may further include a radiation emitter to emit radiation toward the plurality of collimators and an image processor to generate a radiological image based on the electric signals from the sensor.

In accordance with a further aspect of the present invention, a collimator module may include a first collimator having a plurality of openings, to receive radiation, and a second collimator having a plurality of openings, to receive radiation having passed through the first collimator. At least one of the first collimator and the second collimator may be movable or rotatable relative to the other collimator. When a high-resolution mode is selected, the first collimator or the second collimator may be moved or rotated to reduce a size of a passage region that allows radiation to pass through the first collimator and the second collimator, and when a high-sensitivity mode is selected, the first collimator or the second collimator may be moved or rotated to increase the size of the passage region.

In accordance with a further aspect of the present invention, a radiological imaging apparatus may include a radiation emitter to emit radiation, a first collimator having a plurality of openings, to receive radiation emitted from the radiation emitter, a second collimator having a plurality of openings, to receive radiation having passed through the first collimator, a sensor to sense radiation having passed through the first collimator and the second collimator and to change the sensed radiation into electric signals, an image processor to generate a radiological image based on the electric signals from the sensor, and a controller to selectively control movement or rotation of at least one of the first collimator or the second collimator. When a high-resolution mode is selected, the first collimator or the second collimator may be controlled to move or rotate to reduce a size of a passage region that allows radiation to pass through the first collimator and the second collimator, and when a high-sensitivity mode is selected, the first collimator or the second collimator may be controlled to move or rotate to increase the size of the passage region.

In accordance with a further aspect of the present invention, a collimator module may include a plurality of collimators having a plurality of openings to receive radiation, wherein the plurality of collimators is stacked one above another to allow the radiation to sequentially pass through the plurality of openings, and at least one collimator of the plurality of collimators is movable or rotatable relative to another collimator. The at least one collimator may be moved or rotated to reduce a size of a passage region, through which radiation having passed through the object passes, when a high-resolution mode is selected. The at least one collimator may be moved or rotated to increase the size of the passage region when a high-sensitivity mode is selected.

In accordance with a further aspect of the present invention, a radiological imaging apparatus may include a radiation emitter to emit radiation, a plurality of collimators having a plurality of openings, to receive radiation emitted from the radiation emitter, a sensor to sense radiation having passed through the plurality of collimators and to change the sensed radiation into electric signals, an image processor to generate a radiological image based on the electric signals from the sensor, and a controller to selectively control movement or rotation of at least one collimator among the plurality of collimators. When a high-resolution mode is selected, a size of a passage region that allows radiation to pass through the plurality of collimators is reduced, and when a high-sensitivity mode is selected, the size of the passage region is increased. The plurality of collimators may be stacked one above another to allow the radiation to sequentially pass through the plurality of openings.

In accordance with a further aspect of the present invention, a radiological imaging apparatus may include a radiation emitter to emit radiation, at least one collimator module, to receive radiation emitted from the radiation emitter, a sensor to sense radiation having passed through the at least one collimator module and to change the sensed radiation into electric signals, and an image processor to generate a radiological image based on the electric signals from the sensor. The collimator module may be controlled such that a size of a passage region that allows radiation to pass through at least one collimator, is reduced or increased. The radiological imaging apparatus may further include a controller to control the size of the passage region to be reduced if a selected radiation imaging mode is a high-resolution mode, and to be increased if a selected radiation imaging mode is a high-sensitivity mode. The at least one collimator module may include a stack of a plurality of collimators having a plurality of openings, at least one collimator among the plurality of collimators is movable or rotatable relative to another collimator, and the radiation sequentially passes through the plurality of openings of the plurality of collimators. The collimator module may include a plurality of collimators having a plurality of openings, the openings of the plurality of collimators may have different sizes, and the positions of the collimators may be switchable such that a selected collimator among the plurality of collimators is located in a path of radiation.

In accordance with a further aspect of the present invention, a method of controlling a radiological imaging apparatus may include setting a radiation imaging mode to any one of a high-resolution mode or a high-sensitivity mode, and controlling a collimator module to adjust a size of a passage region that allows radiation to pass through the collimator module, wherein the size of the passage region is reduced if the high-resolution mode is set, and the size of the passage region is increased if the high-sensitivity mode is set. The collimator module may include a plurality of collimators having a plurality of openings to receive radiation, the plurality of collimators is stacked one above another to allow the radiation to sequentially pass through the plurality of openings, and at least one collimator among the plurality of collimators is movable or rotatable relative to another collimator, and wherein the at least one collimator among the plurality of collimators is moved or rotated to increase or reduce the size of the passage region that allows the radiation to pass through the collimator module.

In accordance with a further aspect of the present invention, a collimator module may include a first collimator having a plurality of openings to receive radiation, and a second collimator, disposed next to the first collimator, having a plurality of openings to receive radiation having passed through the first collimator. The first collimator and the second collimator may be operable to receive a control signal to move or rotate about with respect to one another, to adjust a size of a passage region that allows radiation to pass through the first collimator and the second collimator.

The collimator module may further include a third collimator, wherein the collimator module is operable to receive a control signal to change the passage region by positioning the third collimator along a path that allows radiation to pass through the third collimator and one of the first collimator and the second collimator.

The first collimator and the second collimator may move or rotate simultaneously. The collimator module may receive a control signal which drives at least one of the first collimator and second collimator by a movement distance set according to a user command or according to a predetermined distance amount. The control signal may drive at least one of the first collimator and second collimator by a movement distance set according to a predetermined distance amount which is based on a width size of an opening of the first collimator and a width size of an opening of the second collimator.

The control signal may drive at least one of the first collimator and second collimator in at least one of a lateral direction, diagonal direction, clockwise direction, or counterclockwise direction. The first collimator may be stacked directly next to the second collimator, and the control signal may drive at least one of the first collimator and second collimator in a direction to space the first and second collimator apart from one another. The width of the openings of the first collimator may be different from a width of the openings of the second collimator. The height of a partition forming an opening of the first collimator may be different from a height of a partition forming an opening of the second collimator.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1A:
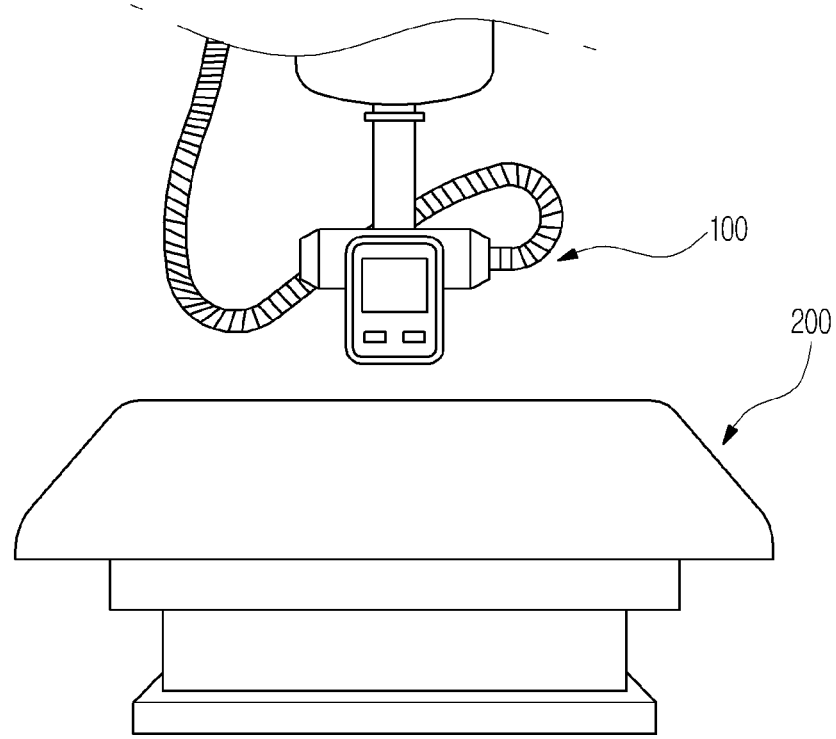
FIGS. 1A to 1C are views respectively illustrating a radiological imaging apparatus according to an embodiment of the present invention.

Reference will now be made in detail to the embodiments of the present invention, examples of which are illustrated in the accompanying drawings, wherein like reference numerals refer to like elements throughout.

Hereinafter, a collimator module, a radiation detector using the collimator module, and a radiological imaging apparatus using the collimator module according to embodiments of the present invention will be described with reference to FIGS. 1A to 8.

FIGS. 1A to 10 illustrate embodiments of a radiological imaging apparatus.

As illustrated in FIG. 1A, according to an embodiment of the present invention, a radiological imaging apparatus may be a Digital Radiography (DR) apparatus that includes a radiation emitter 100 that generates radiation and emits the radiation to an object ob, and a radiation detector 200 that detects radiation having passed through the object ob. In this case, assuming that the radiological imaging apparatus is a table-shaped X-ray imaging apparatus as illustrated in FIG. 1A, the object ob may be placed on the top of the radiation detector 200.

Figure 1B:
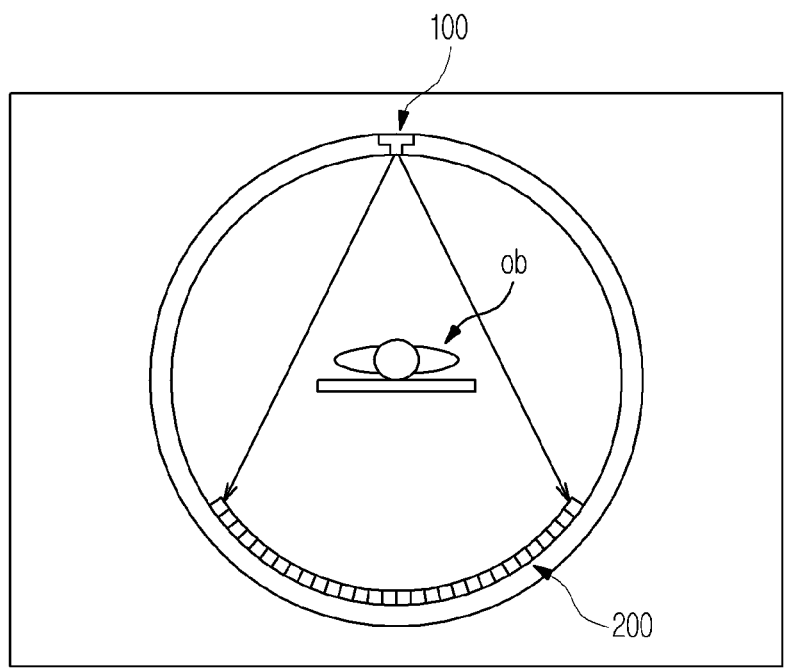
Figure 1C:
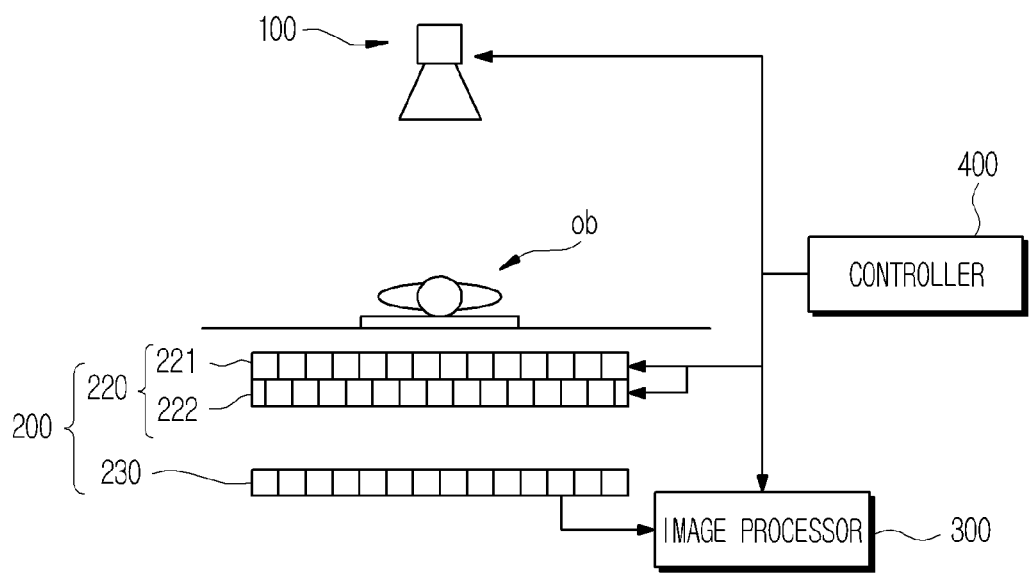

As illustrated in FIG. 1B, according to an embodiment of the present invention, a radiological imaging apparatus may be a computed tomography apparatus. Likewise, the radiological imaging apparatus, e.g., the computed tomography apparatus, includes the radiation emitter 100 that generates radiation and emits the radiation to an object ob, and the radiation detector 200 that detects radiation having passed through the object ob. In this case, the radiation emitter 100 and the radiation detector 200 may be arranged to face each other to capture a radiological image of the object ob at various angles via rotation thereof.

Although FIGS. 1A and 1B illustrate the X-ray imaging apparatus and the computed tomography apparatus by way of examples of the radiological imaging apparatus, the radiological imaging apparatus is not limited thereto and the disclosure may be applied to a Full Field Digital Mammography (FFDM) apparatus or other type of radiological imaging apparatus.

According to an embodiment, the radiological imaging apparatus, as illustrated in FIG. 10, may include an image processor 300 and a controller 400, in addition to the radiation emitter 100 and the radiation detector 200. Here, the radiation detector 200 may include a collimator module 220 and a sensor 230.

The collimator module 220 may perform filtering of radiation reaching the sensor 230 by adjusting the size of a passage region thereof, through which radiation having passed through the object ob will pass. In other words, the collimator module 220 may control some radiation having passed through the object ob to reach the sensor 230 by increasing or reducing the size of a radiation passage region thereof.

The image processor 300 may function to read out a radiological image from electric signals stored in the sensor 230 and perform desired image processing, for example, post-processing, such as contrast or brightness adjustment, on the read-out radiological image.

The controller 400 may control various functions of the radiation emitter 100 or the radiation detector 200, for example. In particular, the controller 400 may generate a control instruction for movement or rotation of at least one of a plurality of collimators 221 and 222 of the collimator module 220, and may transmit the control instruction to the at least one collimator, thereby controlling the size of a radiation passage region of the collimator module 220. In particular, according to embodiments, the controller 400 enables automated adjustment in the size of a radiation passage region according to a radiation imaging mode.

The radiation emitter 100 may include a radiation generation module to generate radiation. The radiation generation module may include a radiation tube that generates radiation having energy corresponding to a voltage applied thereto, for example, X-rays, and a power source that applies a predetermined voltage to the radiation tube.

Considering the radiation generation principle of the radiation generation module in detail, when a predetermined voltage is applied from the power source to the radiation tube, electrons in the radiation tube are accelerated by the applied voltage, and thereafter are rapidly reduced near an anode, causing generation of radiation based on the conservation of energy.

Once radiation has been generated, the radiation emitter 100 emits the generated radiation to the object ob.

The radiation emitted to the object ob may pass through the object ob to thereby reach the radiation detector 200, or may directly reach the radiation detector 200 without passing through the object ob.

Figure 2:
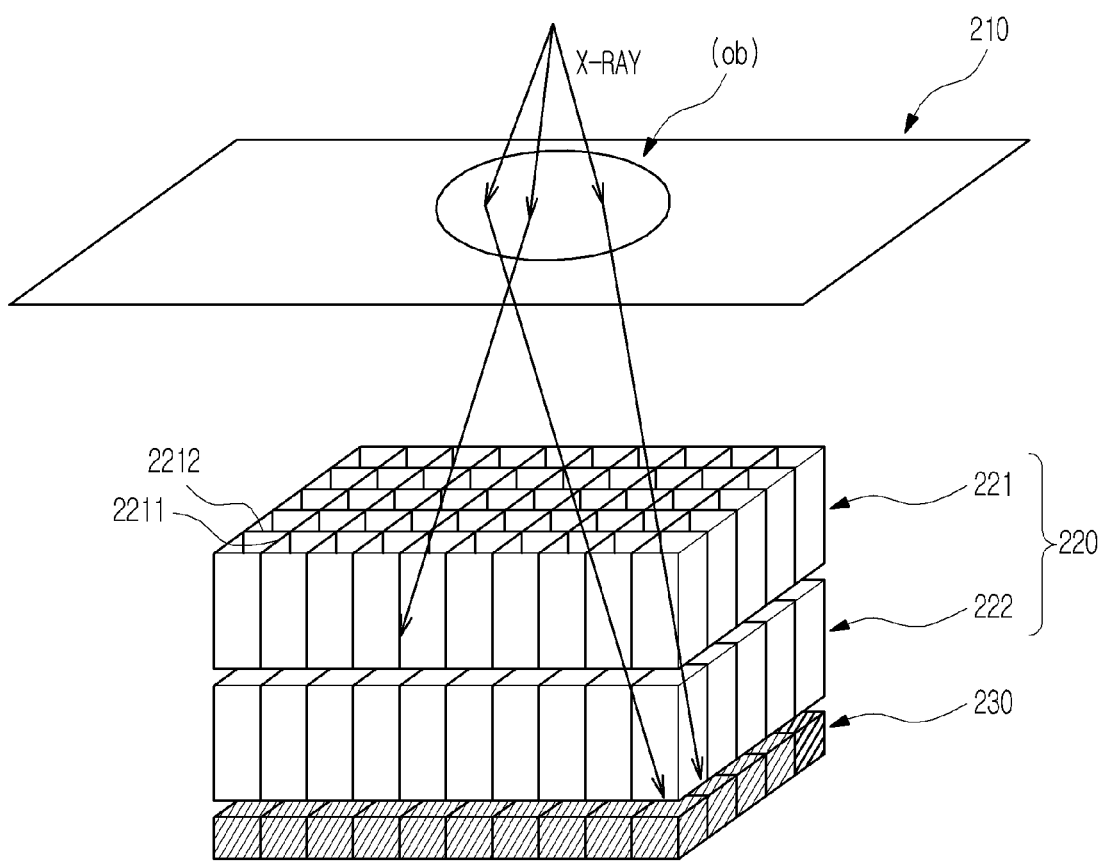
FIG. 2 is a view illustrating a radiation detector according to an embodiment of the present invention.
Figure 3:
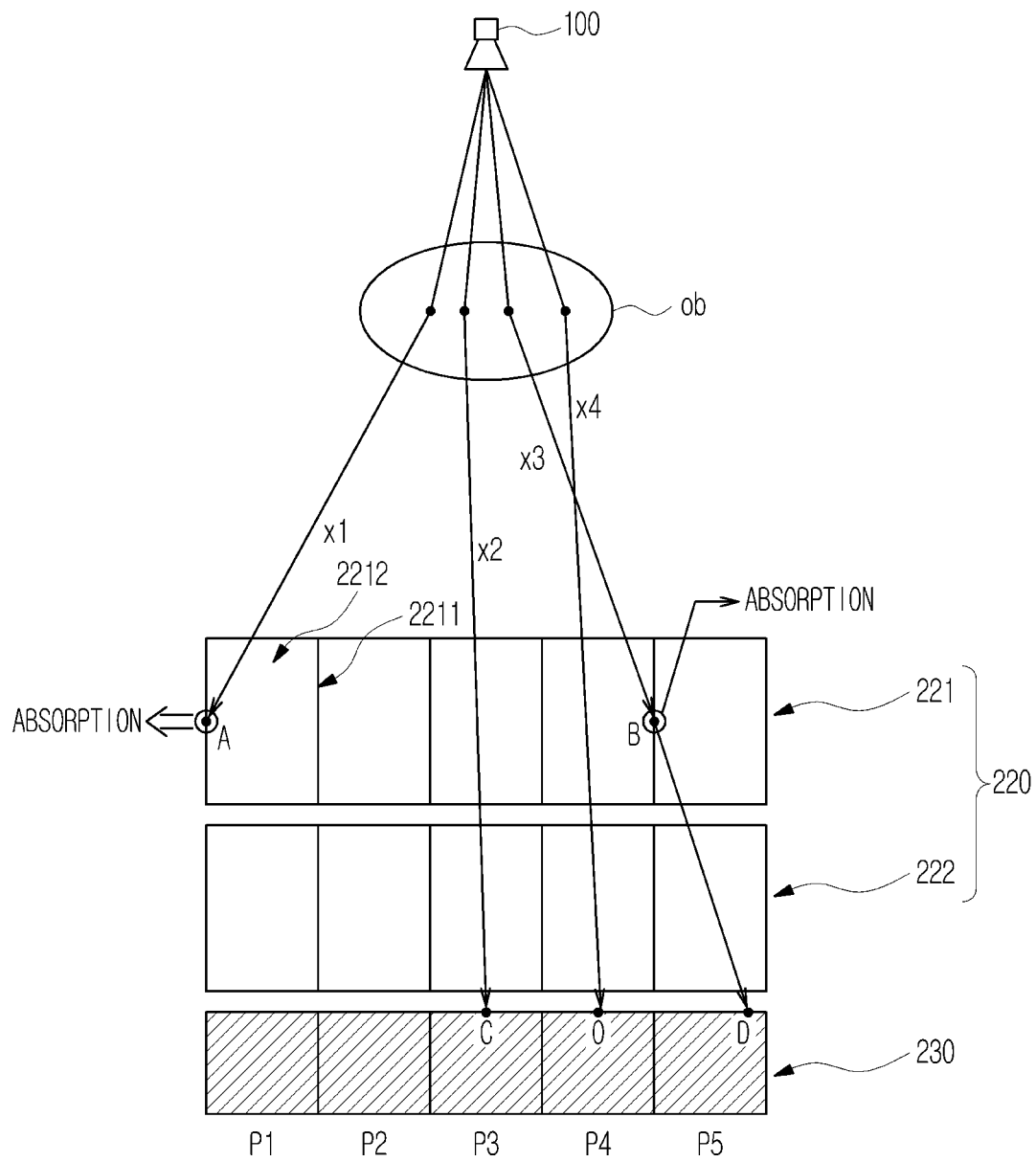
FIG. 3 is a view illustrating a collimator module according to an embodiment of the present invention.

FIGS. 2 and 3 are views illustrating an embodiment of the radiation detector.

According to an embodiment of the present invention, the radiation detector 200, as illustrated in FIG. 2, includes a cradle 210 on which the object ob is placed, the collimator module 220 located below the cradle 210, and the sensor 230 located below the collimator module 220. That is, relative to a device which emits the radiation, received radiation may first pass through the cradle 210, then the collimator module 220, and then the sensor 230.

The cradle 210, on which the object ob is placed, is formed of a high radiation-transmittance material, to allow radiation, for example, X-rays having passed through the object ob or directed to the cradle 210 to reach the sensor 230.

The collimator module 220 may include a plurality of collimators, for example, two collimators 221 and 222 as illustrated in FIG. 2.

The collimators 221 and 222 perform radiation filtering to allow only particular directional radiation having passed through the object ob to reach the sensor 230 and provide the radiation with directivity. That is, it may be possible not only to prevent radiation, scattered while passing through the object ob, from reaching the sensor 230, but also to allow only appropriate radiation to reach the sensor 230, which results in an improved image quality.

To achieve radiation filtering and directivity, the collimators 221 and 222, as illustrated in FIG. 2, include a plurality of partitions 2211 and 2212 formed of, e.g., lead (Pb), to absorb radiation photons. The plurality of partitions 2211 and 2212 absorb radiation, thereby allowing only radiation in a particular range and direction to reach the sensor 230.

More specifically, as illustrated in FIG. 3, radiation x1 to x4 emitted from the radiation emitter 100 reaches the sensor 230 after passing through the object ob.

Radiation having passed through the object ob may be refracted or scattered, as represented by x1 and x3, according to the nature or structure of internal tissues. Accordingly, when the sensor 230 receives the scattered radiation x1 or x3, this means that the sensor 230 receives radiation having passed through unwanted tissues different from desired internal tissues of the object ob, which causes deterioration in the accuracy of a radiological image.

In this case, by arranging the collimators 221 and 222 having openings defined by the plurality of partitions 2211 and 2212 in front of the sensor 230, the scattered radiation x1 or x3 collides with the partitions 2211 and 2212 of the collimators 221 and 222 (as represented by A or B), whereby photons of the radiation x1 or x3 are absorbed by the partitions 2211 and 2212. Only radiation x2 or x4 (i.e. primary photons), which are directed in a particular direction, for example, to the ground rather than being scattered, passes through the openings of the plurality of collimators 221 and 222, thereby reaching a position on the sensor 230, for example, a position C or O.

Otherwise, if the collimators 221 and 222 are not installed in front of the sensor 230, for example, the scattered radiation x3 may be directed to a position D not corresponding to a position of desired internal tissues, which causes deterioration in the accuracy of an image.

The radiation having passed through the openings of the collimator module 220 is received by respective pixels P1 to P5 of the sensor 230, and the sensor 230 changes the radiation into electric signals to store the electric signals.

Figure 4A:
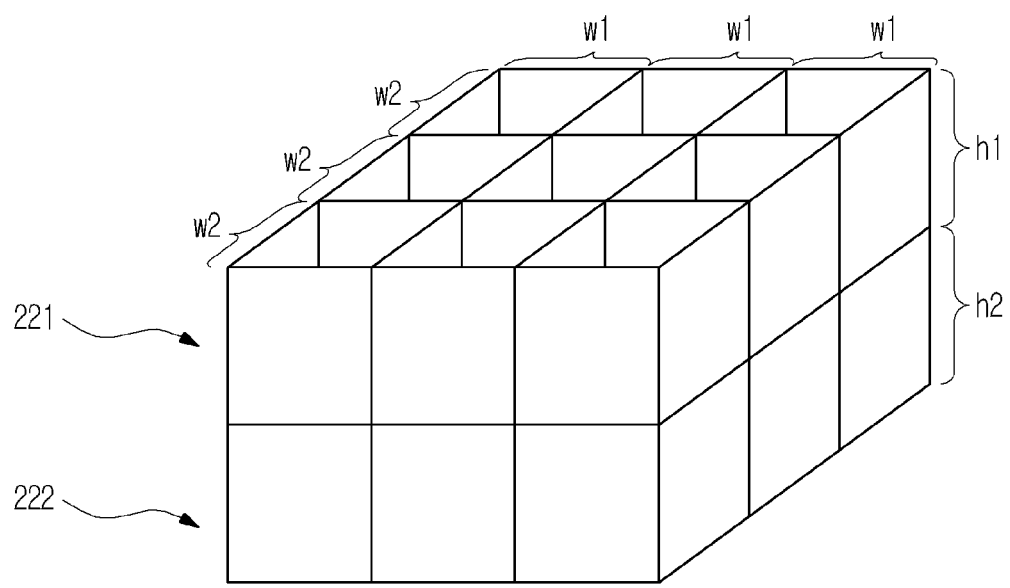
FIGS. 4A to 4C are explanatory views of one embodiment of a collimator module.
Figure 4B:
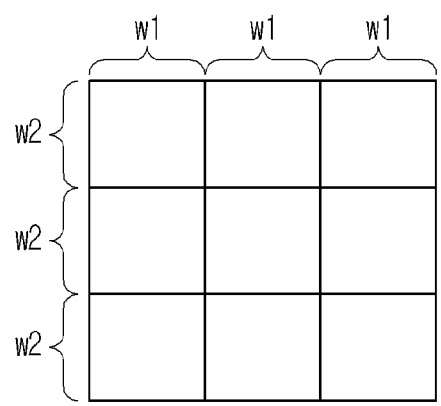
Figure 4C:
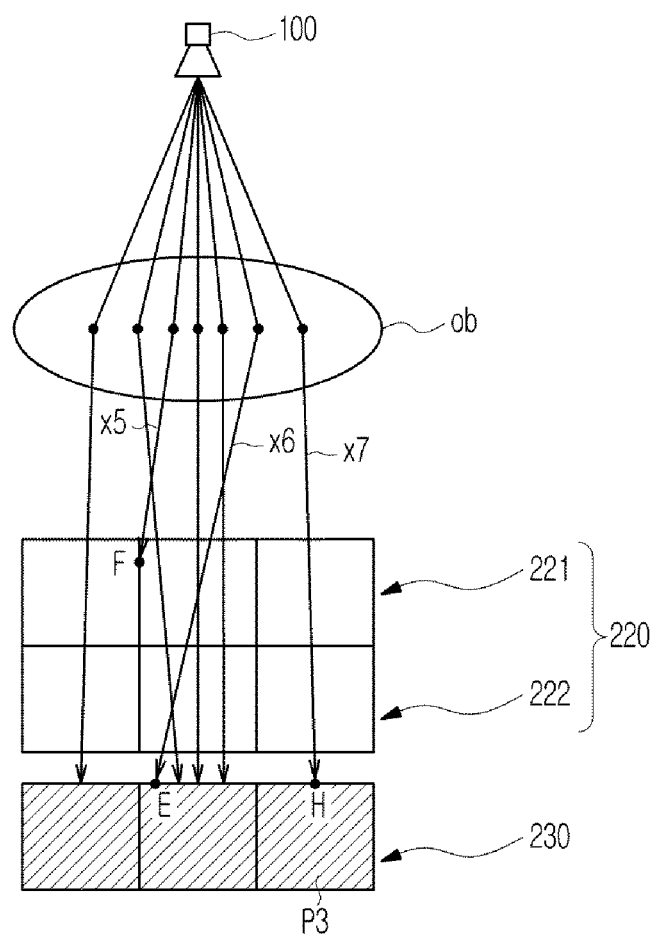

FIGS. 4A to 4C are explanatory views of one embodiment of the collimator module.

As illustrated in FIGS. 4A and 4B, according to an embodiment of the present invention, the collimator module 220 may include a plurality of collimators, for example, the first collimator 221 and the second collimator 222. The plurality of collimators may be stacked one above another. That is, the collimator module 220 may include a stack of the plurality of collimators 221 and 222. For example, the second collimator 222 may be located below the first collimator 221, relative to a device which emits radiation toward the sensor 230 (for example, in a downward direction). Alternatively, the second collimator 222 may be located behind the first collimator 221, relative to a device which emits radiation toward the sensor 230 (for example, in a horizontal direction).

At least one collimator of the plurality of collimators of the collimator module 220, for example, the first collimator 221 or the second collimator 222 may include a plurality of openings defined by the partitions 2211 and 2212 having a constant horizontal length w1 and a constant vertical length w2.

According to an embodiment, each collimator, for example, the first collimator 221 or the second collimator 222, as illustrated in FIGS. 4A and 4B, may include openings having the same widths w1 and w2. According to another embodiment, each collimator, for example, the first collimator 221 or the second collimator 222 may have different widths.

According to the embodiment of the present invention, the width w1 or w2 of the openings of the first collimator 221 and the second collimator 222, for example, may be within a range of about 0.5 mm to about 10 mm. Thus, the area of each opening may be within a range of about 0.25 $mm^2$ to about 100 $mm^2$.

If the width w1 or w2 of any one opening of the collimator 221 or 222 is increased, the quantity of radiation passing through the opening, i.e. the number of photons, is increased. Likewise, if the width w1 or w2 of the opening is reduced, the quantity of radiation passing through the opening, i.e. the number of photons, is reduced.

Accordingly, the quantity of radiation that reaches the sensor 230 through the collimator module 220 is determined according to the size of each opening, i.e. the area of each opening of the first collimator 221 and the second collimator 222. In other words, the size of the openings of each collimator 221 or 222 determines the size of a radiation passage region of the collimator module 220 through which radiation having passed through the object ob will pass.

If the width w1 or w2 of the openings of the first collimator 221 or the second collimator 222 constituting the collimator module 220 is increased, the quantity of radiation passing through one opening, i.e. the number of photons, is increased. Consequently, the sensor 230 senses a great quantity (or relatively larger amount) of radiation and changes the radiation into electric signals. Thereby, the quantity of radiation on a per unit pixel basis of the sensor 230 is increased, which ensures acquisition of a greater quantity of information regarding the object ob. That is, a radiological image having a high sensitivity may be acquired.

On the other hand, if the opening has a great width w1 or w2, this may cause some radiation scattered in the object ob, for example, radiation x6 illustrated in FIG. 4C, to be received by the sensor 230. That is, as illustrated in FIG. 4C, in the case of scattered radiation x5 and x6, for example, some radiation x5 may be absorbed by the partitions 2211, 2212 of the first collimator 221 as represented by F.

However, the radiation x6 is not absorbed by the partitions 2211, 2212, but directly passes through the opening because of a wide space between the partitions 2211, 2212, i.e. the great width w1 or w2 of the opening, thereby reaching a position E on the sensor 230. Additionally, in the case of radiation x7 that is expected to reach a position H of a third pixel P3 of the sensor 230 when not subjected to scattering, it may reach an unexpected position, which may cause an image of a particular internal point of the object ob to be formed via an arbitrary pixel other than a corresponding pixel, resulting in deterioration in the accuracy of a radiological image.

The quantity of radiation reaching the sensor 230 may be determined according to heights h1 and h2 of the respective collimators 221 and 222. If the heights h1 and h2 are increased, even slightly scattered radiation may not pass through the respective collimators 221 and 222 and may collide with and be absorbed by the partitions 2211 and 212. Accordingly, although the quantity of radiation on a per pixel basis sensed by the sensor 230 is reduced, a possibility of receiving radiation scattered in the object ob is further reduced, which improves the accuracy of an image.

According to embodiments, for example, the height h1 of the first collimator 221 or the height h2 of the second collimator 222 may be within a range of about 1 mm to about 40 mm.

In conclusion, to reach the sensor 230 below the collimator module 220, radiation having passed through the object ob, as illustrated in FIGS. 3 to 4C, may need to pass through both the opening of the first collimator 221 and the opening of the second collimator 222. The size of a radiation passage region of the collimator module 220, through which radiation having passed through the object ob will pass, is determined according to the widths w1 and w2 of the openings of the first and second collimators 221 and 222 and the heights h1 and h2 of the respective collimators 221 and 222.

According to an embodiment of the present invention, at least one of the plurality of collimators included in the collimator module 220 is movable in one or more directions.

FIGS. 5A to 5F are explanatory views of another embodiment of the collimator module 220. Although FIGS. 5A to 5F assume that the first collimator 221 and the second collimator 222 have the same width, the widths of both the collimators 221 and 222 are not essentially equal to each other, and may differ from each other. Likewise, heights h1, h2 of both the collimators 221 and 222 may be equal to one another, but are not essentially equal to each other, and may instead differ from each other.

As illustrated in FIGS. 5A to 5F, at least one collimator of the collimator module 220, for example, the first collimator 221 may be moved in a given direction d.

In one example, the first collimator 221 is horizontally movable as illustrated in FIGS. 5A to 5F.

Figure 5A:
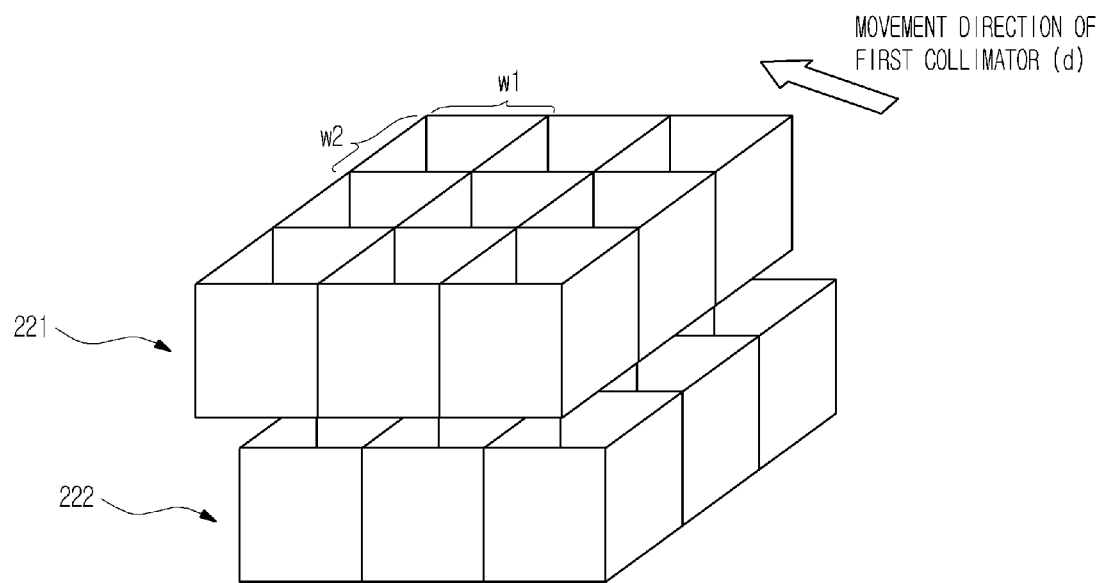
FIGS. 5A to 5F are explanatory views of another embodiment of a collimator module.
Figure 5B:
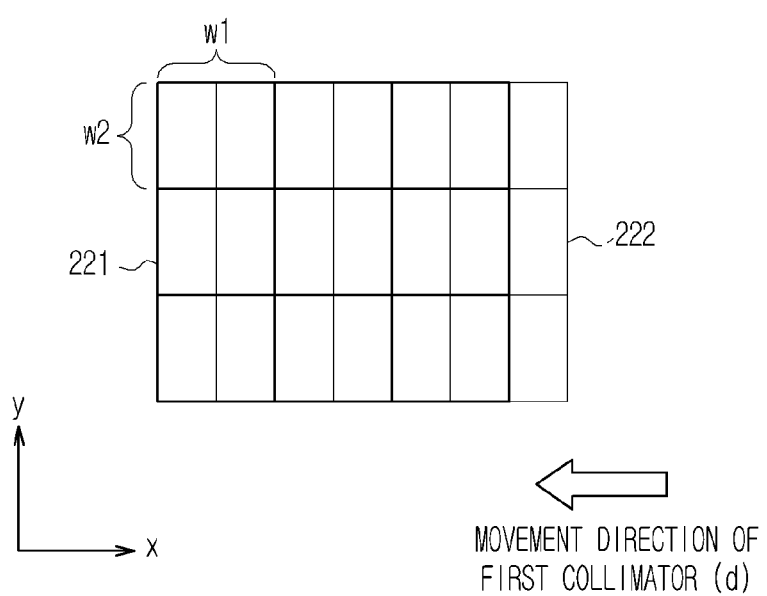

More specifically, as illustrated in FIG. 5B, the first collimator 221 may be moved along the X-axis by a given distance. In this case, the movement distance of the first collimator 221 may be arbitrarily selected by a user or based on preset conditions of the collimator module 220. According to embodiments, the movement distance of the first collimator 221 may be determined within a range that is less than or equal to the smaller of the widths w1, w2 of the first collimator 221 and the second collimator 222. For example, if a first width of the first collimator 221 is smaller than a second width of the second collimator 222, then the movement distance of the first collimator 221 along the X-axis may range between zero and the first width.

Figure 5C:
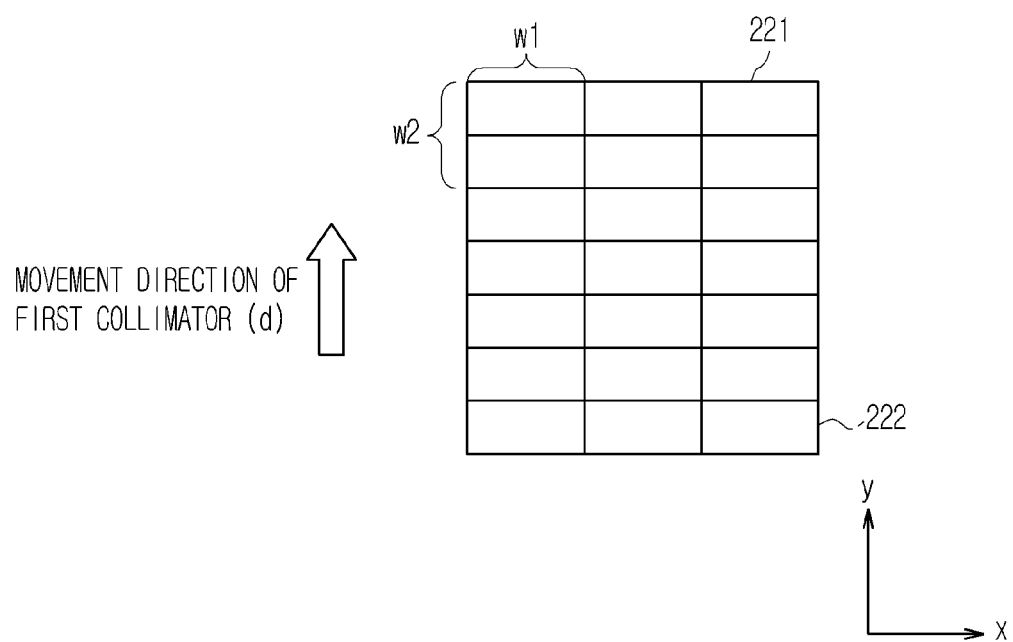

The first collimator 221, as illustrated in FIG. 5C, may be moved along the Y-axis by a given distance. Likewise, the Y-axis movement distance of the first collimator 221 may be arbitrarily selected by a user or based on preset conditions of the collimator module 220. According to embodiments, the Y-axis movement distance of the first collimator 221 may be determined within a range that is less than or equal to the smaller of the widths w1, w2 of the first collimator 221 and the second collimator 222. For example, if a first width of the first collimator 221 is smaller than a second width of the second collimator 222, then the movement distance of the first collimator 221 along the Y-axis may range between zero and the first width.

Figure 5D:
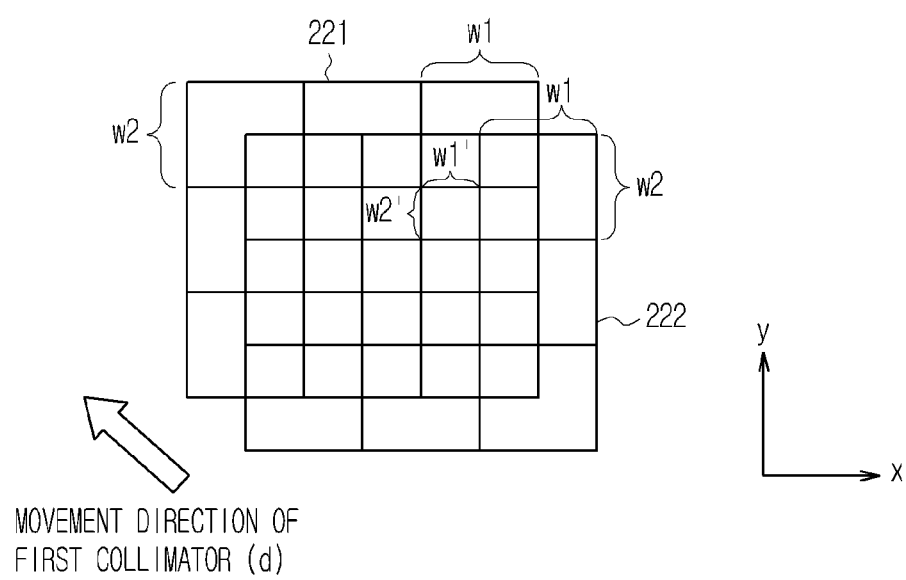

The first collimator 221 may be moved in a diagonal direction as illustrated in FIG. 5D. That is, the first collimator 221 may be moved along both the X-axis and Y-axis. The movement distance of the first collimator 221 may be arbitrarily selected by a user or based on preset conditions of the collimator module 220. Similar to the above-described examples, the movement distance of the first collimator 221 may be determined to be within a predefined range that is based on the widths w1, w2 of the first collimator 221 and the second collimator 222.

Figure 5E:
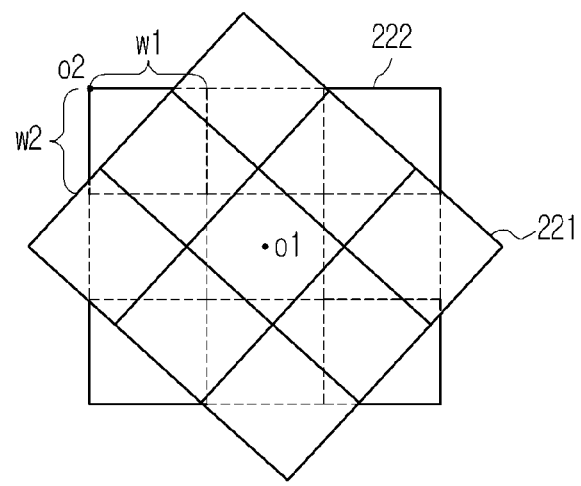

According to embodiments, the first collimator 221, as illustrated in FIG. 5E, may be rotated about a rotating shaft o1, rather than being moved in a particular direction. In this case, the rotating shaft o1, as illustrated in FIG. 5E, may be located at the center of the first collimator 221. Alternatively, the rotating shaft may be located at another particular position of the first collimator 221, for example, at a particular position o2 of an upper left end of the second collimator 222, to allow the first collimator 221 to be rotated about the particular position o2. However, the disclosure is not so limited, and other positions may be selected. The movement distance of the first collimator 221 may be arbitrarily selected by a user or based on preset conditions of the collimator module 220. Similar to the above-described examples, the movement distance of the first collimator 221 may be determined to be within a predefined range that is based on the widths w1, w2 of the first collimator 221 and the second collimator 222.

Likewise, the second collimator 222 may be moved or rotated in a particular direction, in the same manner as the first collimator 221.

Additionally, both the first collimator 221 and the second collimator 222 may be rotated or moved. In this case, both the first collimator 221 and the second collimator 222 may be moved in different directions, for example, in opposite directions.

For example, the first collimator 221 and the second collimator 222 may be simultaneously moved or rotated.

When the first collimator 221 is moved in a horizontal direction, for example, in a movement direction d, or is rotated, the openings of the first collimator 221 and the openings of the second collimator 222 may overlap each other cornerwise as illustrated in FIGS. 5A to 5F.

Radiation having passed through the collimator module 220 may reach the sensor 230 only when passing through both the openings of the first collimator 221 and the second collimator 222. Therefore, when the openings of the first collimator 221 and the openings of the second collimator 222 overlap each other cornerwise as illustrated in FIGS. 5A to 5F, the size of a radiation passage space is reduced. That is, the openings of the first collimator 221 and the openings of the second collimator 222 may overlap each other such that only a portion of an opening of the first collimator 221 and only a portion of an opening of the second collimator 222 overlap with one another. For example, a portion of an opening of the first collimator 221 may overlap with a portion of a plurality of openings of the second collimator 222. For example, a portion of an opening of the first collimator 221 may not overlap with any of the openings of the second collimator 222.

That is, if the first and second collimators 221 and 222 are arranged such that the openings thereof coincide with each other as illustrated in FIGS. 4A and 4B, the widths of a radiation passage region, through which radiation having passed through the object ob will pass, are equal to the widths w1 and w2 of the respective collimators 221 and 222. If the collimators 221 and 222 overlap each other cornerwise, the widths of the radiation passage region, as illustrated in FIG. 5D, are reduced to w1' and w2' that are widths of a space defined by the overlapped collimators 221 and 222.

Figure 5F:
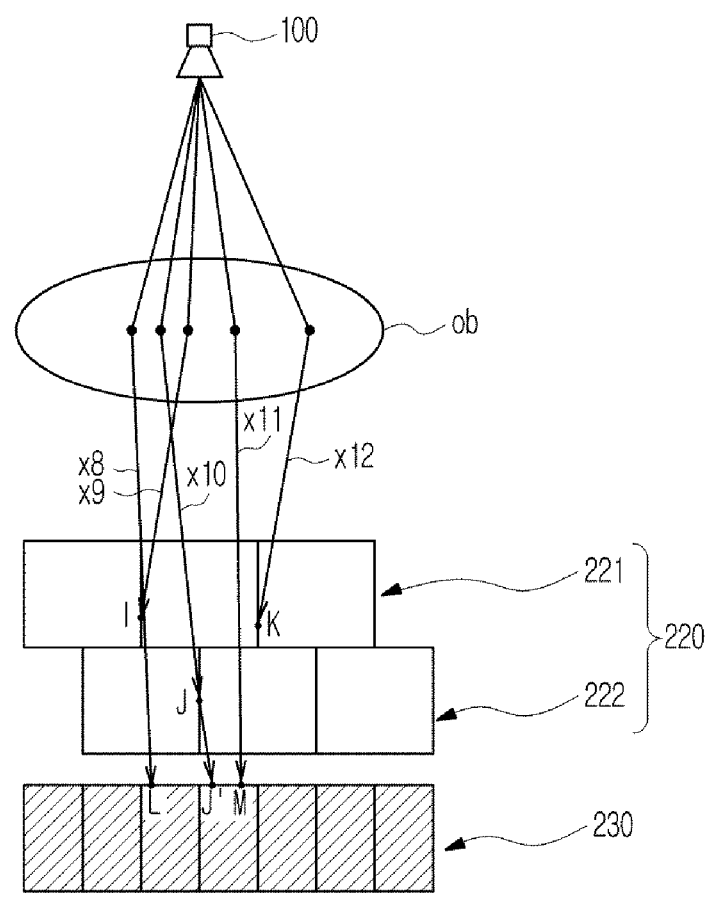

Referring to FIG. 5F, radiation scattered in the object ob may be absorbed by partitions I and K of the first collimator 221 as in the case of radiation x9 and x12, or may be absorbed by a partition J of the second collimator 222 even after passing through the first collimator 221 as in the case of radiation x10. Only appropriate radiation that is not subjected to scattering, for example, primary photons of radiation x8 and x11 may reach the sensor 230 (see L and M).

If the first and second collimators 221 and 222 are arranged such that the openings thereof coincide with each other as illustrated in FIG. 4C, the aforementioned radiation x10 may reach a position on a fourth pixel P4 of the sensor 230 (see J'), causing deterioration in the accuracy of a radiological image.

As illustrated in FIGS. 5A to 5F, when at least one of the collimators 221 and 222 of the collimator module 220 is moved, this causes a reduced quantity of radiation to pass through the collimator module 220 and allows only radiation of accurate information to reach the sensor 230. That is, the sensitivity of an image is deteriorated as the quantity of radiation on a per unit pixel basis of the sensor 230 is reduced, whereas the accuracy of an image is enhanced owing to sensing of only primary photons rather than photons corresponding to scattered radiation. In addition, an enhanced resolution of a radiological image may be achieved, and an increase in the number of pixels per unit area, i.e. a reduction in the size of a pixel, may be achieved.

As described above, if the collimator module 220 is set as illustrated in FIGS. 4A to 4C, a radiological image having high sensitivity, low accuracy and large pixels, may be acquired. On the other hand, if the collimator module 220 is set as illustrated in FIGS. 5A to 5F, i.e. if at least one collimator of the collimator module 220 is moved, a radiological image having lower sensitivity, higher accuracy and smaller pixels, may be acquired relative to the embodiments of FIGS. 4A to 4C.

Accordingly, the sensitivity and accuracy of a radiological image may be adjusted through one collimator module 220, which enables acquisition of various radiological images without replacement of the collimator module 220. This may reduce an economical burden.

Figure 6A:
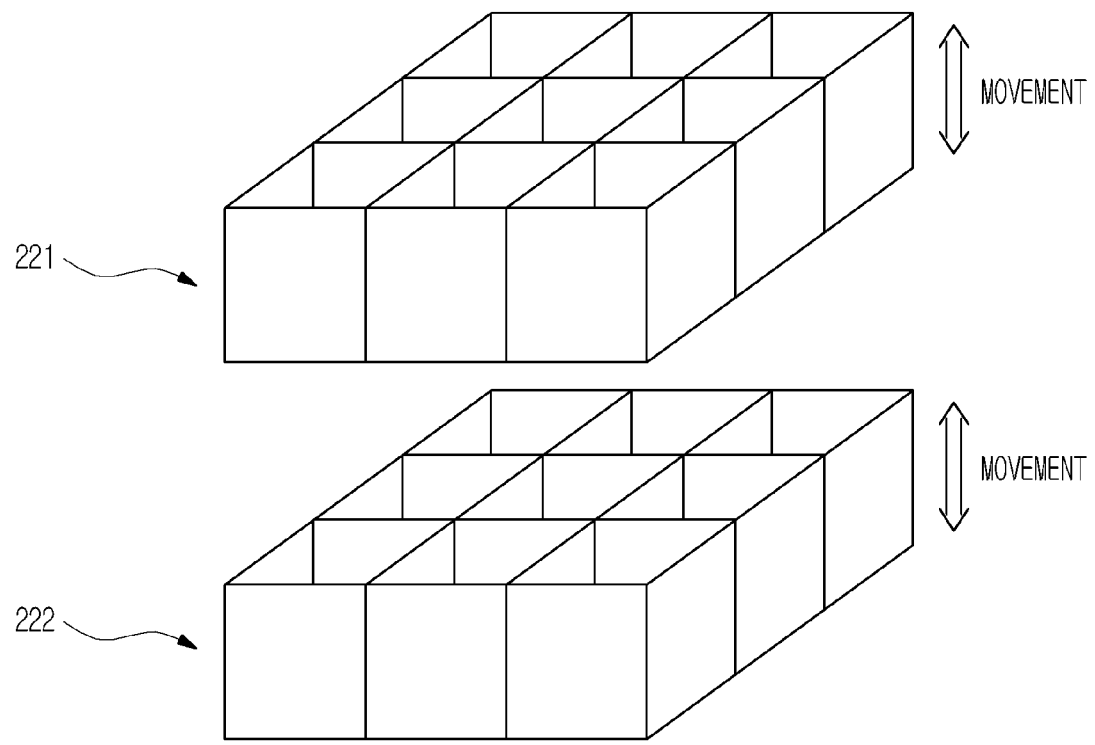
FIGS. 6A and 6B are explanatory views of a further embodiment of a collimator module.
Figure 6B:
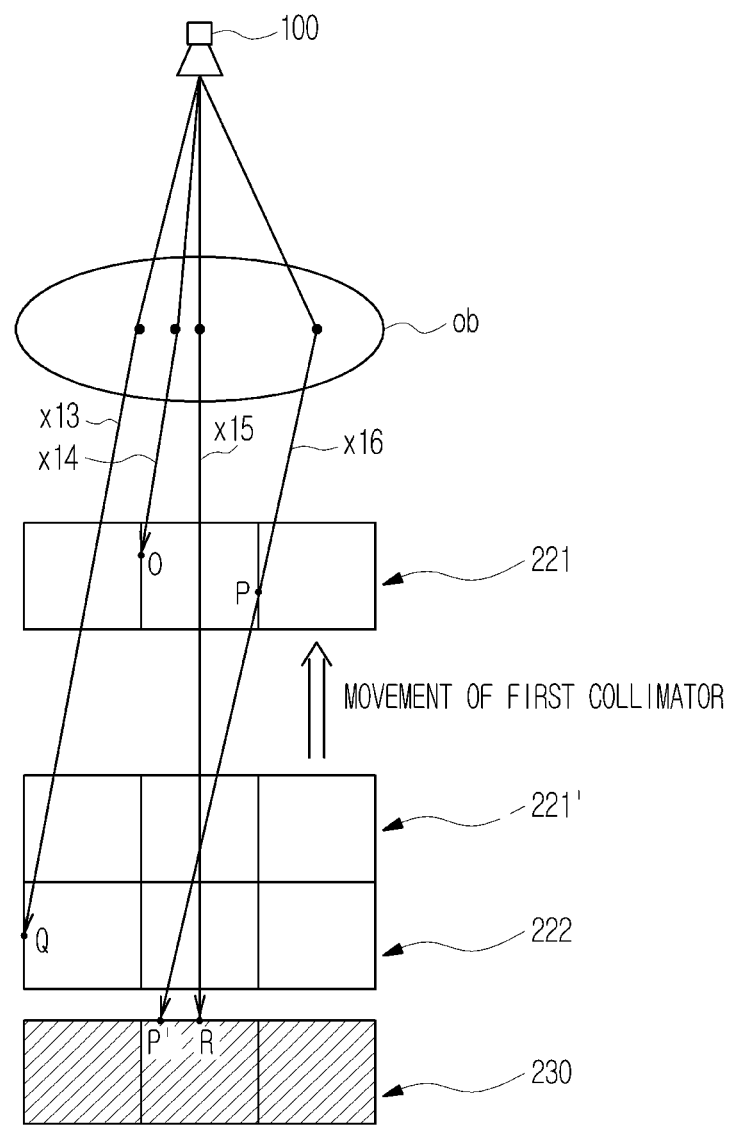

FIGS. 6A and 6B are explanatory views of an embodiment of the collimator module.

According to a further embodiment of the present invention, as illustrated in FIGS. 6A and 6B, at least one of a plurality of collimators of the collimator module 200, for example, the first collimator 221 or the second collimator 222 may be vertically moved. As such, the plurality of collimators, for example, the first collimator 221 and the second collimator 222 may be spaced apart from each other.

As illustrated in FIG. 6B, for example, if the first collimator 221 is vertically moved and is spaced apart from the second collimator 222, this may facilitate easier removal of scattered radiation and assist the sensor 230 in receiving only accurate radiation, i.e. primary photons.

Of radiation x13 to x16 in FIG. 6B, the radiation x13, x14 and x16, which is scattered or not directed to the sensor 230, may be absorbed respectively at a position Q of the second collimator 222 and positions O and P of the first collimator 221, and only the radiation x15 may reach a point R of the sensor 230.

If no movement of the first collimator 221 occurs, the scattered radiation x16 is not absorbed by the partition of the first collimator 221' before movement as well as the partition of the second collimator 222, and thereby arrives at the sensor 230 at position P', which may make it impossible to acquire an accurate image. However, by moving the first collimator 221, removal of the scattered radiation x16 may be possible, resulting in acquisition of an accurate image.

Figure 7:
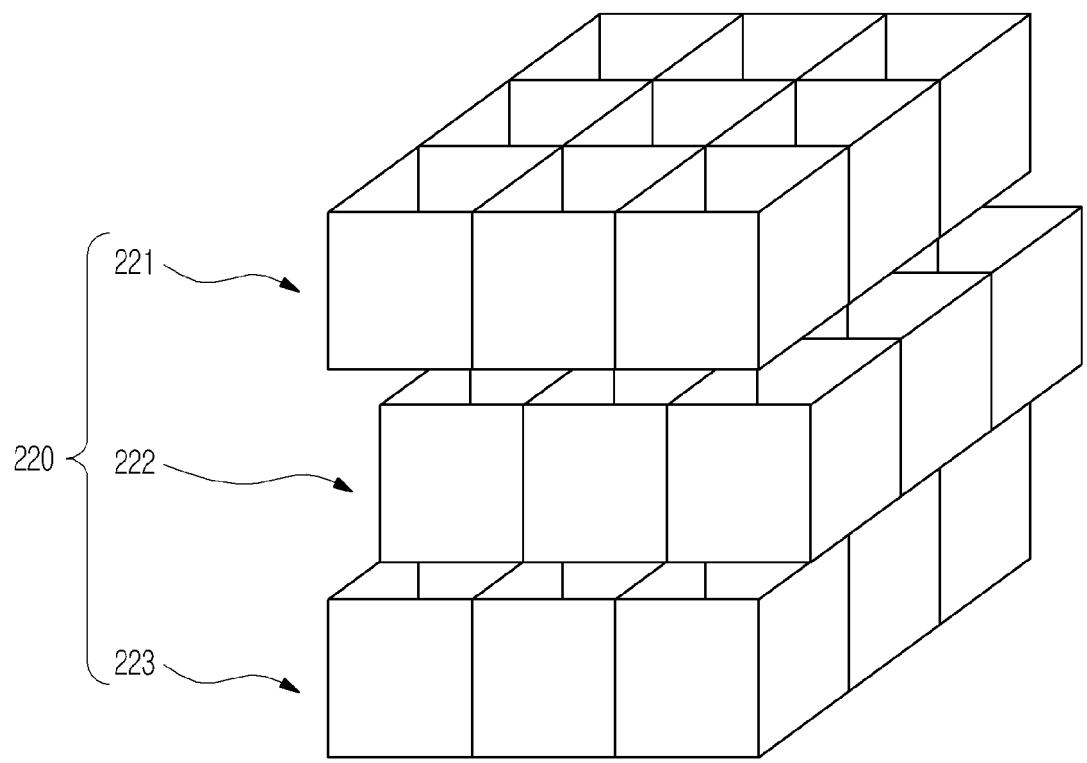
FIG. 7 is an explanatory view of an embodiment of a collimator module.

FIG. 7 is an explanatory view of an embodiment of the collimator module.

According to another embodiment of the present invention, as illustrated in FIG. 7, the collimator module 220 may include a plurality of collimators 221 to 223, and each of the collimators 221 to 223 may be movable relative to the other collimators 221 to 223. That is, on the basis of FIG. 7, the first collimator 221 may be movable laterally, the second collimator 222 may not be movable, and the third collimator 223 may be movable in a forward direction. Additionally, as illustrated in FIG. 6A, the respective collimators 221 to 223 are vertically movable so as to be spaced apart from one another. However, FIG. 7 is merely an example, and the plurality of collimators 221 to 223 may be moveable with respect to one another in different directions.

In the case in which the collimator module 220 includes two, three or more collimators 221 to 223, it may be possible to adjust the size of a radiation passage region in various ways according to movement of the collimators 221 to 223, and to allow a greater quantity of radiation to pass through a partial region of the collimator module 220 and a lesser quantity of radiation to pass through another partial region of the collimator module 220.

As described above, operations of the respective collimators 221 to 223 of the collimator module 220 may be controlled manually by the user, or may be controlled in response to a control instruction transmitted from the above-described controller 400.

According to an embodiment, the collimator module 220 may be selectively driven in response to a control instruction of the controller 400 that is generated according to a selected imaging mode.

For example, if an imaging mode is set to a high-resolution mode, the controller 400 generates a control instruction to operate at least one collimator of the plurality of collimators 221 to 223 of the collimator module 220 as illustrated in FIGS. 5A to 5E. Thereby, in response to the control instruction, at least one collimator of the plurality of collimators 221 to 223 of the collimator module 220, for example, the first collimator 221 is subjected to operation, for example, movement or rotation as illustrated in FIGS. 5A to 5E. As a result, the respective collimators, for example, the first collimator 221 and the second collimator 222 overlap each other cornerwise, causing a reduction in the widths of a radiation passage region. This prevents scattered radiation from passing through the collimator module 220 and assists the sensor 230 in receiving only appropriate radiation. In this way, the accuracy and resolution of an image are enhanced in a high-resolution imaging mode.

Conversely, if an imaging mode is set to a high-sensitivity mode, the controller 400 generates a control instruction to operate at least one collimator among the plurality of collimators 221 to 223 of the collimator module 220 in a manner opposite to that in the high resolution mode. Thereby, in response to the control instruction, the plurality of collimators 221 to 223, for example, the first collimator 221 and the second collimator 222 are arranged to coincide with each other as illustrated in FIGS. 4A and 4B. As a result, the width of a radiation passage region is greater than that in the high-resolution mode. Accordingly, the collimator module 220 may pass a greater quantity of radiation, which allows the sensor 230 to receive a greater quantity of radiation than in the high-resolution mode. In this way, a high-sensitivity radiological image may be acquired in a high-sensitivity imaging mode.

According to an embodiment of the present invention, the collimator module 220 includes a plurality of collimators 221 to 223 having a plurality of openings. If any one collimator among the plurality of collimators 221 to 223 is selected, the selected collimator is controlled so as to be positioned in a path, along which radiation having passed through the object reaches the sensor 230. In other words, the plurality of collimators 221 to 223 within the collimator module 220 may be replaced with each other, i.e. be switched. In this case, the respective collimators may have different sizes of openings. More specifically, the openings of any one collimator within the collimator module 220 may be smaller or greater than the openings of other collimators. Accordingly, the size of the openings of the collimator for passage of radiation may be changed according to whether any one of the plurality of collimators 221 to 223 of the collimator module 220 is positioned on a radiation path, which enables adjustment in the size of a radiation passage region.

In this way, radiation, which has been emitted by the radiation emitter 100 and has passed through the object ob to thereby pass through a region of the collimator module 220, for example, a passage region defined by the openings of the first collimator 221 and the openings of the second collimator 222, reaches the sensor 230.

Figure 8:
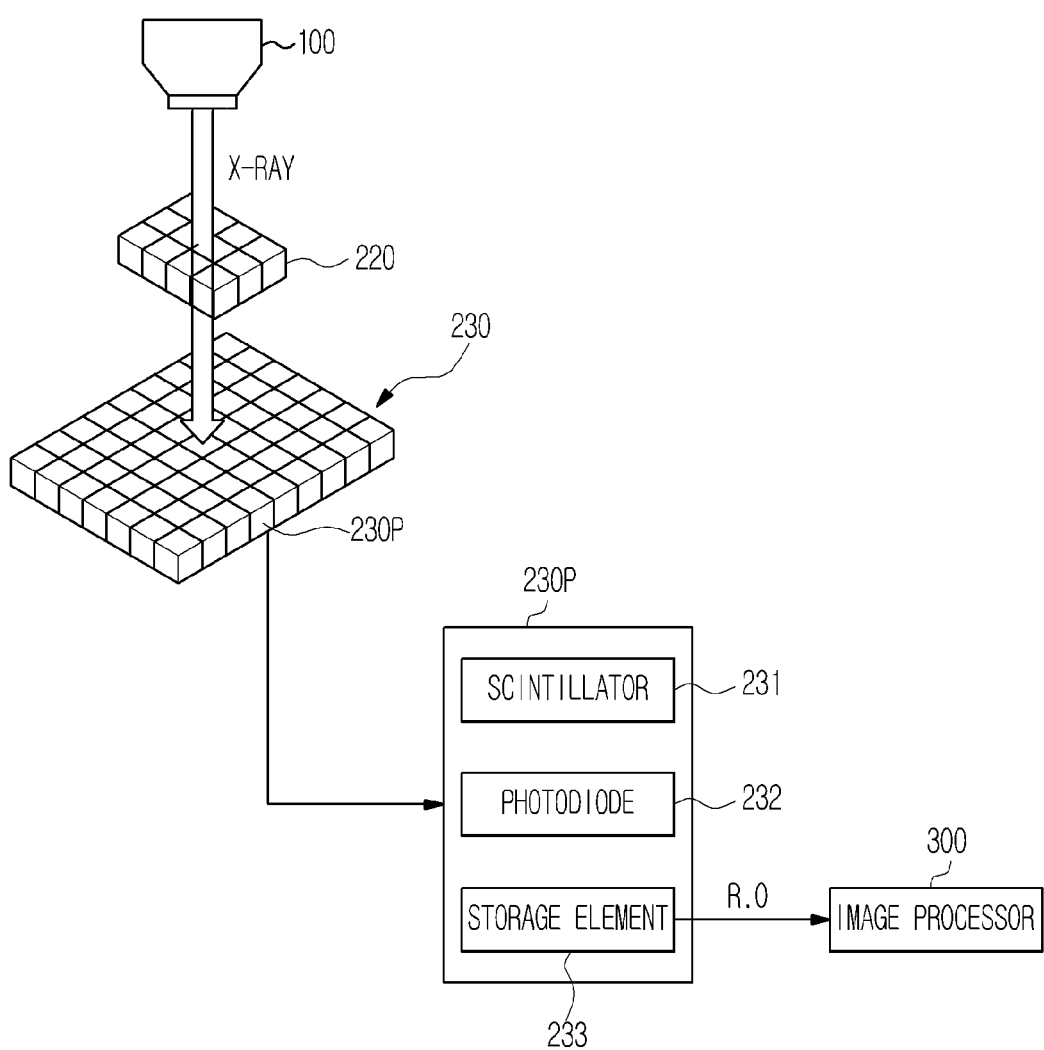
FIG. 8 is an explanatory view of image processing of a radiological imaging apparatus.

FIG. 8 is an explanatory view of image processing of the radiological imaging apparatus.

As illustrated in FIG. 8, the sensor 230 may include a plurality of pixels 230P, and each pixel 230P may include a scintillator 231, a photodiode 232, and a storage element 233. The scintillator 231 glows when hit by radiation, and outputs photons by sensing radiation having passed through the collimator module 220. The photodiode 232 senses the photons output from the scintillator 231 and changes the photons into electric energy to output electric signals for a radiological image. The storage element 233, for example, may be a capacitor which stores the electric signals output from the photodiode 232.

The image processor 300 reads out the electric signals stored in the storage element 233, and thereafter generates a radiological image via image processing. The generated radiological image may be displayed on a display device, such as a monitor. In this case, as described above, the sensitivity, resolution and accuracy of the radiological image may be changed according to relative positions of the plurality of collimators 221 to 223 of the collimator module 220.

The image processor 300 may be a processor of the radiation detector 200, or may be a processor of an external information processing apparatus connected to the radiation detector 200 in a wired or wireless communication network, or a combination thereof.

Figure 9:
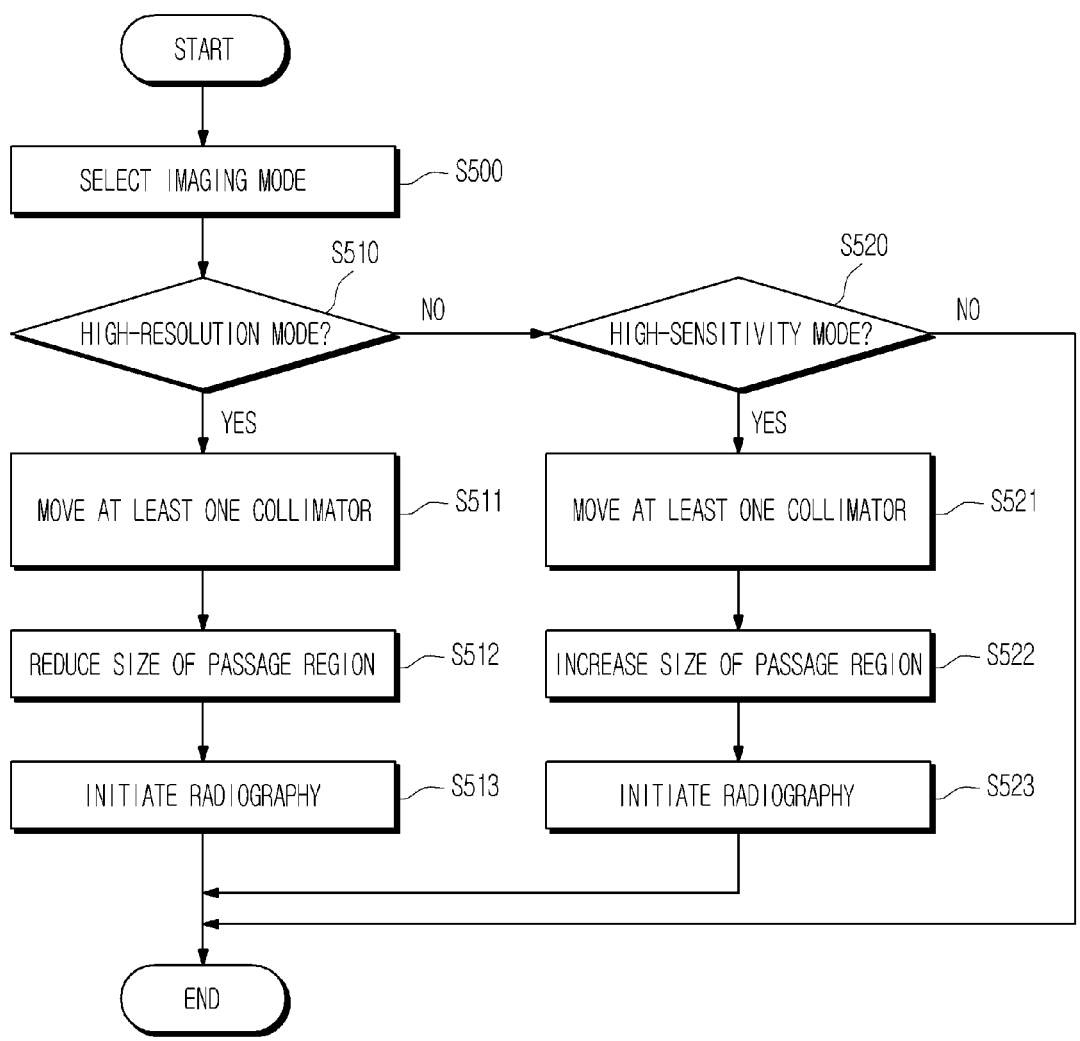
FIG. 9 is a flowchart of a control method of a radiological imaging apparatus according to an embodiment.

FIG. 9 is a flowchart of a control method of a radiological imaging apparatus according to an embodiment.

According to an embodiment of the present invention, after any one radiation imaging mode is selected from among various radiation imaging modes as necessary, imaging of the object may be performed according to the selected radiation imaging mode.

As illustrated in FIG. 9, in a method of imaging an object in a selected radiation imaging mode, first, any one imaging mode, for example, a high-resolution imaging mode or a high-sensitivity imaging mode may be selected from among a plurality of imaging modes (S500). This selection may be performed by the user, or may be preset according to an object or an imaging region of the object.

Then, the size of a passage region of a collimator module installed between a cradle and a sensor is adjusted according to the selected radiation imaging mode. The passage region of the collimator module passes some radiation having passed through the object, but filters out some radiation, for example, scattered radiation.

For example, the size of the passage region of the collimator module may be reduced if a high-resolution mode is selected, and is increased if a high-sensitivity mode may be selected.

According to an embodiment of the present invention, the collimator module includes a plurality of collimators having a plurality of openings through which radiation having passed through the object passes. The plurality of collimators may be stacked one above another (or side by side in a horizontal arrangement) such that radiation sequentially passes through the plurality of openings. At least one collimator among the plurality of collimators may be moved or rotated relative to the other collimator.

If a high-resolution mode is selected (S510), at least one collimator among the plurality of collimators of the collimator module may be moved in a given direction so as to overlap the other collimator cornerwise (S511), which results in a reduction in the size of the passage region (S512).

If radiography is initiated (S513), an accurate high-resolution image is generated owing to a reduced size of the passage region of the collimator module. However, the image has a relatively low sensitivity compared to the high-sensitivity mode because the absolute quantity of radiation received by the sensor is reduced.

If a high-sensitivity mode is selected (S520), at least one collimator among the plurality of collimators of the collimator module is moved in a given direction so as to coincide with the other collimator as illustrated in FIG. 4A, rather than overlapping the other collimator cornerwise (S521), which results in an increase in the size of the passage region (S522).

If radiography is initiated (S523), the sensor receives a greater quantity of radiation owing to an increased size of the passage region of the collimator module. Accordingly, an image having a relatively high sensitivity compared to the high-resolution mode may be acquired. However, as described above, the accuracy of the image may be deteriorated due to scattered radiation.

According to another embodiment of the present invention, the collimator module may include a plurality of collimators having different sizes of openings, any one of the plurality of collimators may be selected according to an imaging mode, and the selected collimator may be moved so as to be positioned in a path of radiation having passed through the object. In the case of a high-resolution imaging mode, the collimator having a smaller size of openings is moved so as to be positioned in the path of radiation having passed through the object. In the case of a high-sensitivity imaging mode, the collimator having a greater size of openings is moved so as to be positioned in the radiation path. That is, switching between the plurality of collimators of the collimator module is performed according to a radiation imaging mode.

As is apparent from the above description, with provision of a collimator module, a radiation detector using the collimator module, and a radiological imaging apparatus using the collimator module, appropriate radiation may be detected according to imaging purpose.

In particular, it may be possible to change the size of a radiation passage region in response to a user request by moving at least one collimator among a plurality of collimators stacked one above another, which allows the radiation detector to receive and detect radiation suitable for generation of a radiological image.

Accordingly, a radiological image having a sensitivity or resolution optimized for a desired imaging purpose may be acquired.

In addition, it may be possible to reduce radiation exposure of the patient's body by adjusting the generation or emission quantity of radiation and the position of the collimator module according to a desired imaging purpose.

Provision of the collimator module to freely adjust the size of the passage region may achieve economical effects including reduced manufacturing costs.

Here it is noted that the radiological imaging apparatus, collimator modules, and control methods according to the example embodiments disclosed herein may be applied to a target object including a human, an animal, or other life form, or to any other objects for which radiological imaging may be applied (e.g., security applications such as airport security or border security, industrial applications such as taking x-ray images of welds, art applications such as taking x-ray images of paintings, etc.).

The radiological imaging apparatus and methods according to the above-described example embodiments may use one or more processors, which may include a microprocessor, central processing unit (CPU), digital signal processor (DSP), or application-specific integrated circuit (ASIC), as well as portions or combinations of these and other processing devices.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

The methods for controlling a radiological imaging apparatus and/or collimator module according to the above-described embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules that are recorded, stored, or fixed in one or more computer-readable storage media, in order to perform the operations of the above-described embodiments, or vice versa. The program instructions may be executed by one or more processors. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

Although the example embodiments of the present invention have been shown and described, it would be appreciated by those skilled in the art that changes may be made to these embodiments without departing from the principles and spirit of the invention, the scope of which is defined in the claims and their equivalents.

What is claimed is:

1. A collimator module comprising:
a first collimator having a plurality of openings, to receive radiation; and
a second collimator having a plurality of openings, to receive radiation having passed through the first collimator,
wherein
the second collimator is stacked directly next to the first collimator, and
at least one of the first collimator and the second collimator is movable or rotatable relative to the other collimator.

2. The collimator module according to claim 1, wherein
a passage region is formed by at least an opening among the plurality of openings of the first collimator and at least an opening among the plurality of openings of the second collimator, and
a size of the passage region that allows radiation to pass through the first collimator and the second collimator is adjusted according to movement or rotation of the first collimator or the second collimator.

3. The collimator module according to claim 1, wherein at least one of the first collimator and the second collimator is movable or rotatable such that some of the plurality of openings of the first collimator and some of the plurality of openings of the second collimator deviate from each other.

4. The collimator module according to claim 1, wherein the first collimator or the second collimator is moved toward or away from the second collimator or the first collimator.

5. The collimator module according to claim 1, wherein the first collimator or the second collimator further comprises a plurality of partitions, and
the plurality of openings of the first collimator or the second collimator are separated from one another by the plurality of partitions.

6. The collimator module according to claim 1, wherein the plurality of openings of the first collimator and the second collimator have the same size.

7. The collimator module according to claim 1, wherein a width of each opening of the plurality of openings of the first collimator and the second collimator is within a range of 0.5 mm to 10 mm.

8. The collimator module according to claim 1, wherein a height of the first collimator or the second collimator is within a range of 1 mm to 40 mm.

9. A radiation detector comprising:
a first collimator having a plurality of openings, to receive radiation;
a second collimator having a plurality of openings, to receive radiation having passed through the first collimator, wherein the second collimator is stacked directly next to the first collimator; and
a sensor to sense radiation having passed through the first collimator and the second collimator and to change the sensed radiation into electric signals,
wherein the first collimator or the second collimator is movable or rotatable relative to the second collimator or the first collimator.

10. The radiation detector according to claim 9, wherein
a passage region is formed by at least an opening among the plurality of openings of the first collimator and at least an opening among the plurality of openings of the second collimator, and
a size of the passage region that allows radiation to pass through the first collimator and the second collimator is adjusted according to movement or rotation of the first collimator or the second collimator.

11. The radiation detector according to claim 9, wherein the first collimator or the second collimator is movable or rotatable relative to the second collimator or the first collimator such that some of the plurality of openings of the first collimator and some of the plurality of openings of the second collimator overlap each other.

12. The radiation detector according to claim 9, wherein the first collimator or the second collimator is moved toward or away from the second collimator or the first collimator.

13. A radiological imaging apparatus comprising:
a radiation emitter to emit radiation;
a first collimator having a plurality of openings, to receive radiation emitted from the radiation emitter;
a second collimator having a plurality of openings, to receive radiation having passed through the first collimator, wherein the second collimator is stacked directly next to the first collimator;
a sensor to sense radiation having passed through the first collimator and the second collimator and to change the sensed radiation into electric signals;
an image processor to generate a radiological image based on the electric signals from the sensor; and
a controller to control movement or rotation of at least one of the first collimator or the second collimator.

14. The radiological imaging apparatus according to claim 13, wherein the controller controls movement or rotation of at least one of the first collimator or the second collimator according to an object to be imaged, an imaging area of the object, or a preset imaging mode.

15. The radiological imaging apparatus according to claim 13, wherein
a passage region is formed by at least an opening among the plurality of openings of the first collimator and at least an opening among the plurality of openings of the second collimator, and
a size of the passage region that allows radiation to pass through the first collimator and the second collimator is adjusted according to movement or rotation of the first collimator or the second collimator.

16. The radiological imaging apparatus according to claim 13, wherein the first collimator or the second collimator is movable or rotatable relative to the second collimator or the first collimator such that some of the plurality of openings of the first collimator and some of the plurality of openings of the second collimator overlap each other.

17. The radiological imaging apparatus according to claim 13, wherein the first collimator or the second collimator is moved toward or away from the second collimator or the first collimator.

18. The radiological imaging apparatus according to claim 13, wherein the image processor generates a radiological image corresponding to one pixel based on the electric signals derived from radiation having passed through the same openings of the first collimator and the second collimator.

19. A collimator module comprising:
a first collimator having a plurality of openings, to receive radiation; and
a second collimator having a plurality of openings, to receive radiation having passed through the first collimator,
wherein
the second collimator is stacked directly next to the first collimator,
at least one of the first collimator and the second collimator is movable or rotatable relative to the other collimator, and
a passage region is formed by at least an opening among the plurality of openings of the first collimator and at least an opening among the plurality of openings of the second collimator,
wherein, when a high-resolution mode is selected, the first collimator or the second collimator is moved or rotated to reduce a size of the passage region that allows radiation to pass through the first collimator and the second collimator, and
wherein, when a high-sensitivity mode is selected, the first collimator or the second collimator is moved or rotated to increase the size of the passage region.

20. A radiological imaging apparatus comprising:
a radiation emitter to emit radiation;
a first collimator having a plurality of openings, to receive radiation emitted from the radiation emitter;
a second collimator having a plurality of openings, to receive radiation having passed through the first collimator, wherein the second collimator is stacked directly next to the first collimator;
a sensor to sense radiation having passed through the first collimator and the second collimator and to change the sensed radiation into electric signals;
an image processor to generate a radiological image based on the electric signals from the sensor; and
a controller to selectively control movement or rotation of at least one of the first collimator or the second collimator,
wherein
a passage region is formed by at least an opening among the plurality of openings of the first collimator and at least an opening among the plurality of openings of the second collimator,
when a high-resolution mode is selected, the first collimator or the second collimator is controlled to move or rotate to reduce a size of the passage region that allows radiation to pass through the first collimator and the second collimator, and
when a high-sensitivity mode is selected, the first collimator or the second collimator is controlled to move or rotate to increase the size of the passage region.

21. A collimator module comprising:
a first collimator having a plurality of openings to receive radiation; and
a second collimator, disposed next to the first collimator, having a plurality of openings to receive radiation having passed through the first collimator, wherein the second collimator is stacked directly next to the first collimator,
wherein
a passage region is formed by at least an opening among the plurality of openings of the first collimator and at least an opening among the plurality of openings of the second collimator, and
the first collimator and the second collimator are operable to receive a control signal to move or rotate about with respect to one another, to adjust a size of the passage region that allows radiation to pass through the first collimator and the second collimator.

22. The collimator module of claim 21, further comprising a third collimator,
wherein the third collimator is operable to receive a control signal to be positioned along a path that allows radiation to pass through the third collimator and one of the first collimator and the second collimator so that the passage region is changed.

23. The collimator module of claim 21, wherein the first collimator and the second collimator move or rotate simultaneously.

24. The collimator module of claim 21, wherein the control signal drives at least one of the first collimator and the second collimator by a movement distance set according to a user command or according to a predetermined distance amount.

25. The collimator module of claim 21, wherein the control signal drives at least one of the first collimator and the second collimator by a movement distance set according to a predetermined distance amount which is based on a width size of an opening of the first collimator and a width size of an opening of the second collimator.

26. The collimator module of claim 21, wherein the control signal drives at least one of the first collimator and the second collimator in at least one of a lateral direction, diagonal direction, clockwise direction, or counterclockwise direction.

27. The collimator module of claim 21, wherein the control signal drives at least one of the first collimator and the second collimator in a direction to space the first collimator and the second collimator apart from one another.

28. The collimator module of claim 21, wherein a width of each opening of the plurality of openings of the first collimator is different from a width of each opening of the plurality of openings of the second collimator.

29. The collimator module of claim 21, wherein a height of a partition forming an opening of the first collimator is different from a height of a partition forming an opening of the second collimator.

30. A collimator module comprising:
a plurality of collimators, each collimator of the plurality of collimators having a plurality of openings, to receive radiation,
wherein the plurality of collimators are stacked one above another to allow the received radiation to sequentially pass through the plurality of openings, and at least one collimator among the plurality of collimators is movable or rotatable relative to another collimator among the plurality of collimators.

31. A radiological imaging apparatus comprising:
a plurality of collimators, each collimator of the plurality of collimators having a plurality of openings to receive radiation, wherein the plurality of collimators are stacked one above another; and
a sensor to sense radiation having passed through the plurality of collimators and to change the sensed radiation into electric signals,
wherein the plurality of collimators are stacked one above another to allow the received radiation to sequentially pass through the plurality of openings, and at least one collimator among the plurality of collimators is movable or rotatable relative to another collimator.

32. The radiological imaging apparatus according to claim 31, further comprising:
a radiation emitter to emit radiation toward the plurality of collimators; and
an image processor to generate a radiological image based on the electric signals from the sensor.

33. A collimator module comprising:
a plurality of collimators, each collimator of the plurality of collimators having a plurality of openings to receive radiation,
wherein the plurality of collimators are stacked one above another to allow the radiation to sequentially pass through the plurality of openings, and at least one collimator of the plurality of collimators is movable or rotatable relative to another collimator, and
wherein
a passage region is formed by a plurality of openings of the plurality of collimators, and
the at least one collimator is moved or rotated to reduce a size of the passage region, through which radiation having passed through the object passes, when a high-resolution mode is selected, and the at least one collimator is moved or rotated to increase the size of the passage region when a high-sensitivity mode is selected.

34. A radiological imaging apparatus comprising:
a radiation emitter to emit radiation;
a plurality of collimators, each collimator of the plurality of collimators having a plurality of openings, to receive radiation emitted from the radiation emitter, wherein the plurality of collimators are stacked one above another;
a sensor to sense radiation having passed through the plurality of collimators and to change the sensed radiation into electric signals;
an image processor to generate a radiological image based on the electric signals from the sensor; and
a controller to selectively control movement or rotation of at least one collimator among the plurality of collimators,
wherein
a passage region is formed by a plurality of openings of the plurality of collimators, and
when a high-resolution mode is selected, a size of the passage region that allows radiation to pass through the plurality of collimators is reduced, and
when a high-sensitivity mode is selected, the size of the passage region is increased,
wherein the plurality of collimators are stacked one above another to allow the radiation to sequentially pass through the plurality of openings.

35. A radiological imaging apparatus comprising:
a radiation emitter to emit radiation;
at least one collimator module, to receive radiation emitted from the radiation emitter;
a sensor to sense radiation having passed through the at least one collimator module and to change the sensed radiation into electric signals; and
an image processor to generate a radiological image based on the electric signals from the sensor,
wherein
a passage region is formed by at least an opening of the at least one collimator module,
the at least one collimator module is controlled such that a size of the passage region that allows radiation to pass through at least one collimator, is reduced or increased, and
the at least one collimator module includes a stack of a plurality of collimators.

36. The radiological imaging apparatus according to claim 35, further comprising a controller to control the size of the passage region to be reduced if a selected radiation imaging mode is a high-resolution mode, and to be increased if a selected radiation imaging mode is a high-sensitivity mode.

37. The radiological imaging apparatus according to claim 36, wherein
the plurality of collimators have a plurality of openings, and
at least one collimator among the plurality of collimators is movable or rotatable relative to another collimator, and the radiation sequentially passes through the plurality of openings of the plurality of collimators.

38. The radiological imaging apparatus according to claim 36, wherein the at least one collimator module includes a plurality of collimators, each collimator of the plurality of collimators having a plurality of openings, and the plurality of openings of the plurality of collimators have different sizes, and
wherein positions of the plurality of collimators are switchable such that a selected collimator among the plurality of collimators is located in a path of radiation.

39. A method of controlling a radiological imaging apparatus, the method comprising:
setting a radiation imaging mode to any one of a high-resolution mode or a high-sensitivity mode; and
controlling a collimator module to adjust a size of a passage region that allows radiation to pass through the collimator module, wherein the collimator module comprises a plurality of collimators which are stacked one above another,
wherein
the passage region is formed by at least an opening of the at least one collimator module, and
the size of the passage region is reduced if the high-resolution mode is set, and the size of the passage region is increased if the high-sensitivity mode is set.

40. The method according to claim 39, wherein the collimator module includes a plurality of collimators having a plurality of openings to receive radiation, the plurality of collimators are stacked one above another to allow the radiation to sequentially pass through the plurality of openings, and at least one collimator among the plurality of collimators is movable or rotatable relative to another collimator, and
wherein the at least one collimator among the plurality of collimators is moved or rotated to increase or reduce the size of the passage region that allows the radiation to pass through the collimator module.

* * * * *